United States Patent [19]

Lok et al.

[11] Patent Number: 4,956,164

[45] Date of Patent: Sep. 11, 1990

[54] QUINARY MOLECULAR SIEVE COMPOSITIONS

[75] Inventors: Brent M. T. Lok, New City; Bonita K. Marcus, Rye; Edith M. Flanigen, White Plains, all of N.Y.

[73] Assignee: UOP, Des Plaines, Ill.

[21] Appl. No.: 63,791

[22] Filed: Jun. 22, 1987

Related U.S. Application Data

[63] Continuation of Ser. No. 600,168, Apr. 13, 1984, abandoned.

[51] Int. Cl.$^5$ .............................................. C01B 33/28
[52] U.S. Cl. ...................................... 423/306; 423/328
[58] Field of Search ............... 423/305, 306, 326, 328, 423/329; 502/60, 62, 77, 162, 164, 208, 213, 214

[56] References Cited

U.S. PATENT DOCUMENTS

| | | | |
|---|---|---|---|
| 4,310,440 | 1/1982 | Wilson | 423/305 X |
| 4,420,467 | 12/1983 | Whittam | 423/308 |
| 4,440,871 | 4/1984 | Lok et al. | 502/214 |
| 4,486,397 | 12/1984 | Eshraghi et al. | 423/306 |
| 4,500,651 | 2/1985 | Lok et al. | 502/208 |
| 4,567,029 | 1/1986 | Wilson et al. | 502/164 |

FOREIGN PATENT DOCUMENTS

| | | |
|---|---|---|
| 0054364 | 6/1982 | European Pat. Off. |
| 0055046 | 6/1982 | European Pat. Off. |
| 0055529 | 7/1982 | European Pat. Off. |
| 0059059 | 9/1982 | European Pat. Off. |
| 2024790 | 1/1980 | United Kingdom |

OTHER PUBLICATIONS

Schmitz-DuMont, "Zeitschrift fur Anorganische und Allgemeine Chemie" 302, 1955, pp. 121-135.

*Primary Examiner*—Robert L. Stoll
*Assistant Examiner*—R. Bruce Breneman
*Attorney, Agent, or Firm*—Thomas K. McBride; Eugene I. Snyder; Frank S. Molinaro

[57] ABSTRACT

Molecular sieves having three-dimensional microporous framework structures of $CoO_2$, $MnO_2$, $AlO_2$, $PO_2$, and $SiO_2$ tetrahedral oxide units are disclosed. These molecular sieves have an empirical chemical composition on an anhydrous basis are expressed by the formula:

$$mR: (Co_uMn_vAl_xP_ySi_z)O_2$$

wherein "R" represents at least one organic templating agent present in the intracrystalline pore system; "m" represents the molar amount of "R" present per mole of $(Co_uMn_vAl_xP_ySi_z)O_2$; and "u", "v", "x", "y" and "z" represent the mole fractions of cobalt, manganese, aluminum, phosphorus and silicon, respectively, present as tetrahedral oxides. Their use as adsorbents, catalysts, etc. is disclosed.

7 Claims, 3 Drawing Sheets

QUINARY MOLECULAR SIEVE COMPOSITIONS

This application is a continuation of application Ser. No. 600,168, filed Apr. 13, 1984, now abandoned.

FIELD OF THE INVENTION

The instant invention relates to a novel class of crystalline microporous molecular sieves, to the method of their preparation and to their use as adsorbents and catalysts. The invention relates to novel molecular sieves having cobalt and manganese present as tetrahedral oxide units, $MO_2^{-2}$, where "M" is cobalt and manganese, with tetrahedral oxide units of aluminum ($AlO_2^-$), phosphorus ($PO_2^+$) and silicon ($SiO_2$). These compositions may be prepared hydrothermally from gels containing reactive compounds of cobalt, manganese, aluminum, phosphorus and silicon, and preferably at least one organic templating agent which functions in part to determine the course of the crystallization mechanism and the structure of the crystalline product.

BACKGROUND OF THE INVENTION

Molecular sieves of the crystalline aluminosilicate zeolite type are well known in the art and now comprise over 150 species of both naturally occurring and synthetic compositions. In general the crystalline zeolites are formed from corner-sharing $AlO_2$ and $SiO_2$ tetrahedra and are characterized by having pore openings of uniform dimensions, having a significant ion-exchange capacity and being capable of reversibly desorbing an adsorbed phase which is dispersed throughout the internal voids of the crystal without displacing any atoms which make up the permanent crystal structure.

Other crystalline microporous compositions which are not zeolitic, i.e. do not contain $AlO_2$ tetrahedra as essential framework constituents, but which exhibit the ion-exchange and/or adsorption characteristics of the zeolites are also known. Metal organosilicates which are said to possess ion-exchange properties, have uniform pores and are capable of reversibly adsorbing molecules having molecular diameters of about 6Å or less, are reported in U.S. Pat. No. 3,941,871 issued Mar. 2, 1976 to Dwyer et al. A pure silica polymorph, silicalite, having molecular sieving properties and a neutral framework containing neither cations nor cation sites is disclosed in U.S. Pat. No. 4,061,724 issued Dec. 6, 1977 to R. W. Grose et al.

A recently reported class of microporous compositions and the first framework oxide molecular sieves synthesized without silica, are the crystalline aluminophosphate compositions disclosed in U.S. Pat. No. 4,310,440 issued Jan. 12, 1982 to Wilson et al. These materials are formed from $AlO_2$ and $PO_2$ tetrahedra and have electrovalently neutral frameworks as in the case of silica polymorphs. Unlike the silica molecular sieve, silicalite, which is hydrophobic due to the absence of extra-structural cations, the aluminophosphate molecular sieves are moderately hydrophilic, apparently due to the difference in electronegativity between aluminum and phosphorus. Their intracrystalline pore volumes and pore diameters are comparable to those known for zeolites and silica molecular sieves.

In copending and commonly assigned application Ser. No. 400,438, filed July 26, 1982 (now U.S. Pat. No. 4,440,871), there is described a novel class of silicon-substituted aluminophosphates which are both microporous and crystalline. The materials have a three dimensional crystal framework of $PO_2^+$, $AlO_2^-$ and $SiO_2$ tetrahedral units and, exclusive of any alkali metal or calcium which may optionally be present, an as-synthesized empirical chemical composition on an anhydrous basis of:

$$mR: (Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from zero to 0.3; the maximum value in each case depending upon the molecular dimensions of the templating agent and the available void volume of the pore system of the particular silicoaluminophosphate species involved; and "x", "y", and "z" represent the mole fractions of silicon, aluminum and phosphorus, respectively, present as tetrahedral oxides. The minimum value for each of "x", "y", and "z" is 0.01 and preferably 0.02. The maximum value for "x" is 0.98; for "y" is 0.60; and for "z" is 0.52. These silicoaluminophosphates exhibit several physical and chemical properties which are characteristic of aluminosilicate zeolites and aluminophosphates.

In copending and commonly assigned application Ser. No. 480,738, filed Mar. 31, 1983 (now U.S. Pat. No. 4,500,651), there is described a novel class of titanium-containing molecular sieves whose chemical composition in the as-synthesized and anhydrous form is represented by the unit empirical formula:

$$mR: (Ti_xAl_yP_z)O_2$$

wherein "R" represents at least one organic templating agent present in the intracrystalline pore system; "m" represents the moles of "R" present per mole of $(Ti_xAl_yP_z)O_2$ and has a value of between zero and about 5.0; and "x", "y" and "z" represent the mole fractions of titanium, aluminum and phosphorus, respectively, present as tetrahedral oxides.

In copending and commonly assigned application Ser. No. 514,334, filed July 15, 1983 (now U.S. Pat. No. 4,567,029), there is described a novel class of crystalline metal aluminophosphates having three-dimensional microporous framework structures of $MO_2$, $AlO_2$ and $PO_2$ tetrahedral units and having an empirical chemical composition on an anhydrous basis expressed by the formula:

$$mR: (M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3; "M" represents at least one metal of the group magnesium, manganese, zinc and cobalt; "x", "y" and "z" represent the mole fraction of the metal "M", aluminum and phosphorus, respectively, present as tetrahedral oxides.

In copending and commonly assigned application Ser. No. 514,335, filed July 15, 1983 (now U.S. Pat. No. 4,683,217), there is described a novel class of crystalline ferroaluminophosphates having a three-dimensional microporous framework structure of $FeO_2$, $AlO_2$ and $PO_2$ tetrahedral units and having an empirical chemical composition on an anhydrous basis expressed by the formula $mR: (Fe_xAl_yP_z)O_2$ wherein "R" represents at least one organic templating agent present in the intracrystalline pore system; "m" represents the moles of "R" present per mole of $(Fe_xAl_yP_z)O_2$ and has a value of from zero to 0.3; and "x", "y" and "z" represent the mole fraction of the iron, aluminum and phosphorus, respectively, present as tetrahedral oxides.

The instant invention relates to new molecular sieve compositions having framework tetrahedral oxide units of $CoO_2^{-2}$, $MnO_2^{-2}$, $AlO_2^{-}$, $PO_2^{+}$, and $SiO_2$.

SUMMARY OF THE INVENTION

Figure 1:
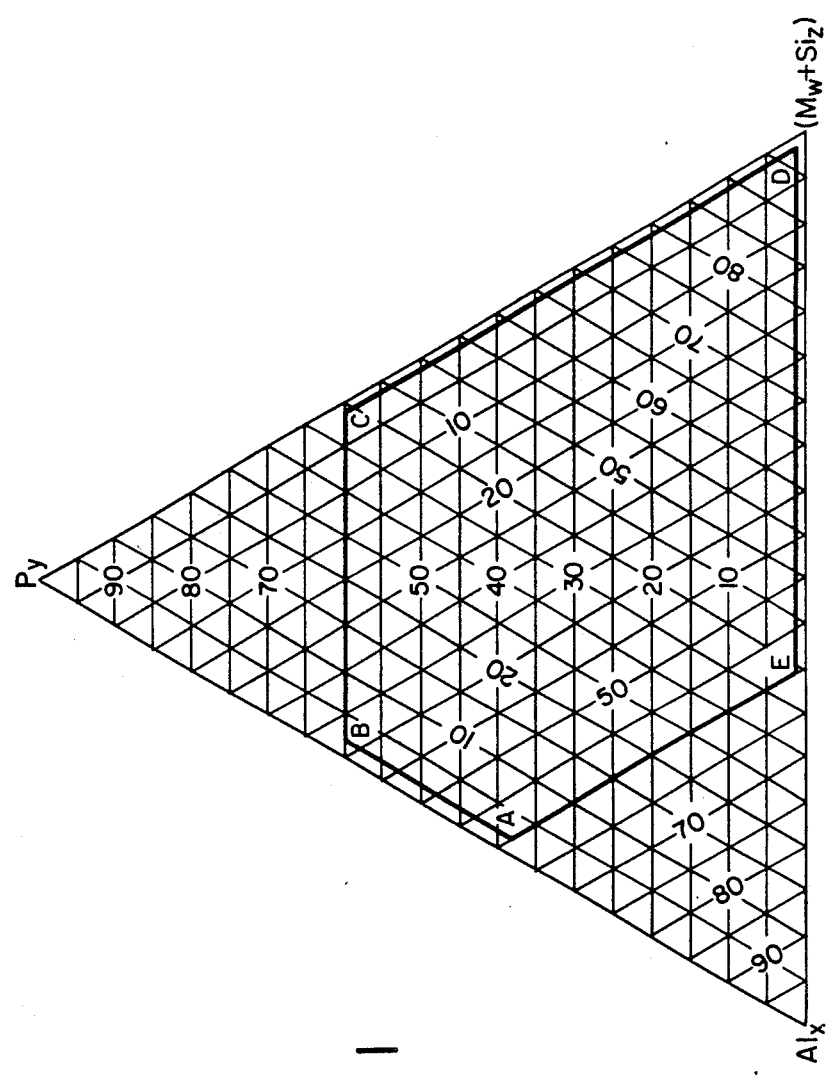
FIG. 1 is a ternary diagram wherein parameters relating to the instant compositions are set forth as mole fractions.

The instant invention relates to a new class of crystalline molecular sieves having a three dimensional microporous framework structures of $CoO_2^{-2}$, $MnO_2^{-2}$, $AlO_2$, $PO_2^{+}$, and $SiO_2$ tetrahedral units. These new molecular sieves exhibit ion-exchange, adsorption and catalytic properties and accordingly find wide use as adsorbents and catalysts. The members of this novel class of compositions have crystal framework structures of $CoO_2^{-2}$, $MnO_2^{-2}$, $AlO_2^{-}$, $PO_2^{+}$, and $SiO_2$ and have an empirical chemical composition on an anhydrous basis expressed by the formula:

$mR: (Co_uMn_vAl_xP_ySi_z)O_2$ wherein "R" represents at least one organic templating agent present in the intracrystalline pore system; "m" represents the molar amount of "R" present per mole of $(Co_uMn_vAl_xP_ySi_z)O_2$ and has a value of zero to about 0.3; and "u", "v", "x", "y" and "z" represent the mole fractions of cobalt, manganese, aluminum, phosphorus and silicon, respectively, present as tetrahedral oxides.

The molecular sieves of the instant invention will be generally referred to herein by the acronym "CoMnAPSO" to designate a framework structure of $SiO_2$, $AlO_2^{-}$, $PO_2^{-}$, $CoO_2^{-2}$ and $MnO_2^{-2}$ tetrahedral oxide units. To identify various structural species which make up each of the subgeneric classes, each species is assigned a number and is identified as "CoMnAPSO-i" where "i" is an integer. The given species designation is not intended to denote a similarity to any other species denomination by a numbering system.

DETAILED DESCRIPTION OF THE INVENTION

The instant invention relates to a new class of molecular sieves having a three-dimensional microporous crystal framework structure of $CoO_2^{-2}$, $MnO_2^{-2}$, $AlO_2^{-}$, $PO_2^{+}$ and $SiO_2$ tetrahedral oxide units. Although the following discussion will generally refer in most instances to $CoO_2^{-2}$, such designation is also meant to include the fact that $CoO_2^{-}$ may also be present. These new molecular sieves exhibit ion-exchange, adsorption and catalytic properties and, accordingly, find wide use as adsorbents and catalysts.

The relative amounts of cobalt, manganese, aluminum, phosphorus and silicon are expressed by the empirical chemical formula (anhydrous):

$mR: (Co_uMn_vAl_xP_ySi_z)O_2$ where "u", "v", "x", "y" and "z" represent the mole fractions of cobalt, manganese, aluminum, phosphorus and silicon, respectively. The CoMnAPSO molecular sieves have an empirical chemical composition on an anhydrous basis expressed by the formula:

$mR: (Co_uMn_vAl_xP_ySi_z)O_2$ wherein "R" represents at least one organic templating agent present in the intracrystalline pore system; "m" represents the molar amount of "R" present per mole of $(Co_uMn_vAl_xP_ySi_z)O_2$ from zero (0) to about 0.3; and "u", "v", "x", "y" and "z" represent the mole fractions of cobalt, manganese, aluminum, phosphorus and silicon, respectively, present as tetrahedral oxides. The mole fractions "u", "v", "x", "y" and "z" are generally defined as being within the pentagonal compositional area defined by points A, B, C, D and E of FIG. 1, where "w" is the sum of "u" and "v" and where "$M_w$" in FIG. 1 represents the combined mole fractions of cobalt and manganese:

| Point | Mole Fraction | | |
|---|---|---|---|
| | x | y | (z + w) |
| A | 0.60 | 0.37 | 0.03 |
| B | 0.37 | 0.60 | 0.03 |
| C | 0.01 | 0.60 | 0.39 |
| D | 0.01 | 0.01 | 0.98 |
| E | 0.60 | 0.01 | 0.39 |

Figure 2:
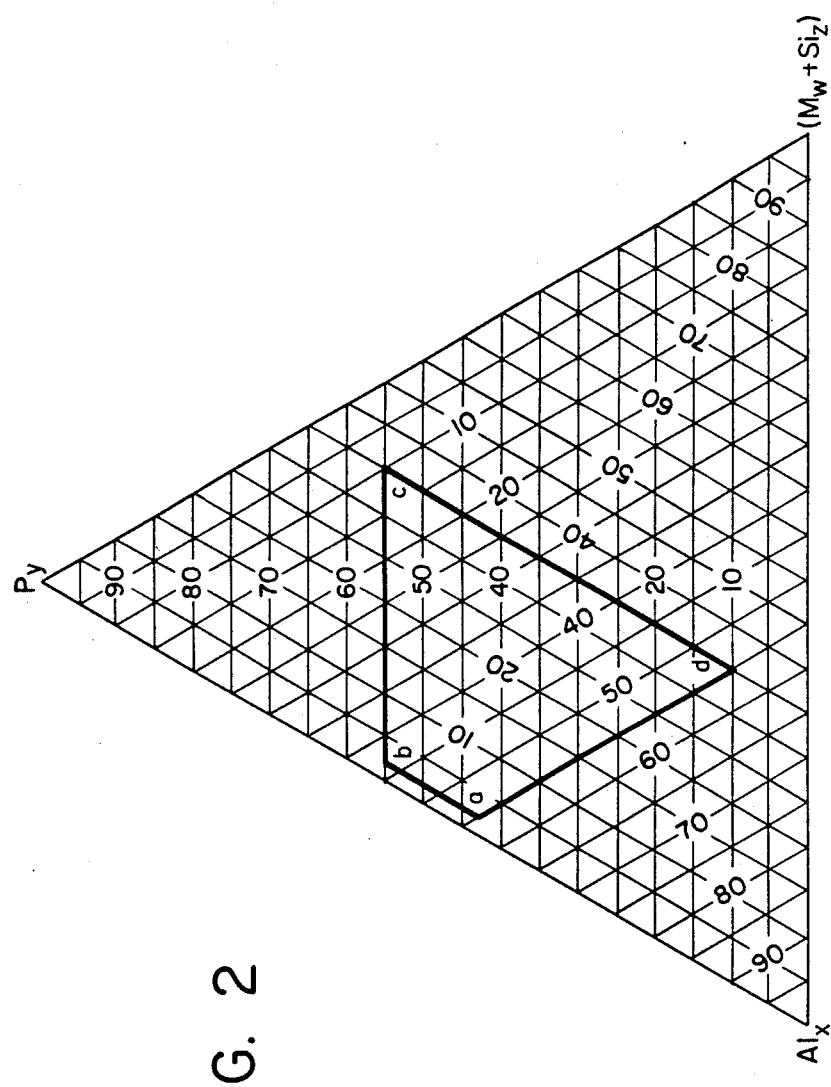
FIG. 2 is a ternary diagram wherein parameters relating to preferred compositions are set forth as mole fractions.

The mole fractions u, v, x, y and z, expressed as in FIG. 1, are preferably defined as being within the tetragonal compositional area defined by points a, b, c and d of FIG. 2 as follows:

| | Mole Fraction | | |
|---|---|---|---|
| | x | y | (z + w) |
| a | 0.55 | 0.42 | 0.03 |
| b | 0.42 | 0.55 | 0.03 |
| c | 0.10 | 0.55 | 0.35 |
| d | 0.55 | 0.10 | 0.35 |

The CoMnAPSOs of this invention are useful as adsorbents, catalysts, ion-exchangers, and the like in much the same fashion as aluminosilicates have been employed heretofore, although their chemical and physical properties are not necessarily similar to those observed for aluminosilicates.

CoMnAPSO compositions are generally synthesized by hydrothermal crystallization from a reaction mixture containing reactive sources of cobalt, manganese, aluminum, phosphorus and silicon and preferably an organic templating agent, i.e., structure-directing, agent. The structure-directing agents are preferably a compound of an element of Group VA of the Periodic Table, and may be an alkali or other metal. The reaction mixture is generally placed in a sealed pressure vessel, preferably lined with an inert plastic material such as polytetrafluoroethylene and heated, preferably under autogenous pressure and at typical effective temperatures between 50° C. and 250° C., preferably between 100° C. and 200° C., until crystals of the CoMnAPSO product are obtained, usually over a period of from several hours to several weeks. Typical effective crystallization times are from about 2 hours to 30 days with from about 4 hours to about 20 days being generally employed to obtain CoMnAPSO products. The product is recovered by any convenient method such as centrifugation or filtration.

In synthesizing the CoMnAPSO compositions of the instant invention, it is preferred to employ a reaction mixture composition expressed in terms of the molar ratios as follows:

$$aR: (Co_oMn_pAl_rP_sSi_t)O_2: bH_2O$$

wherein "R" is an organic templating agent; "a" is the amount of organic templating agent "R" and has a value of from zero to about 6 and is preferably an effective amount within the range of greater than zero (0) to about 6; "b" has a value of from zero (0) to about 500, preferably between about 2 and about 300; and "o", "p", "r", "s", and "t" represent the mole fractions of elements cobalt, manganese, aluminum, phosphorus and silicon, respectively, and each has a value of at least 0.01.

Figure 3:
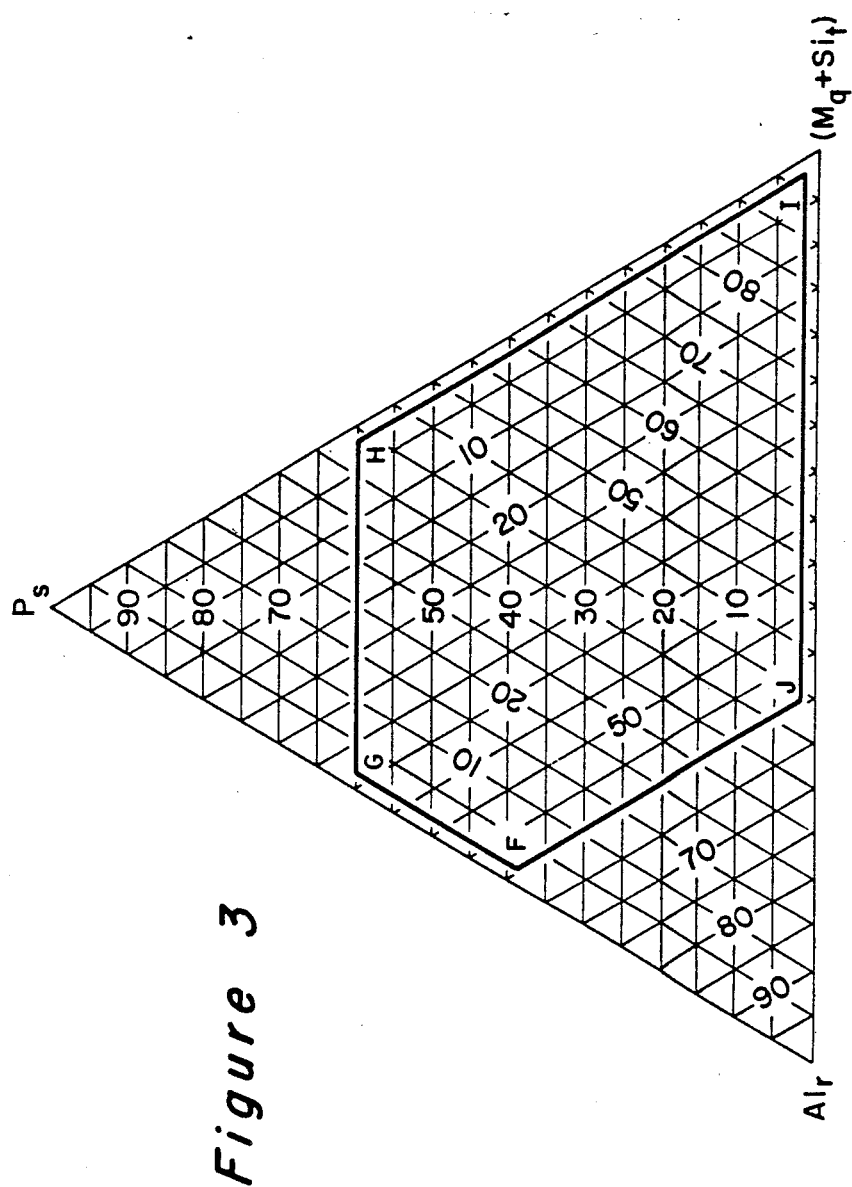
FIG. 3 is a ternary diagram wherein parameters relating to the reaction mixtures employed in the preparation of the compositions of this invention are set forth as mole fractions.

In a preferred embodiment the reaction mixture is selected such that the mole fractions "q", "r", "s" and "t" where "q" is the sum of "o", "p", are generally defined as being within the pentagonal compositional area defined by points E, F, G, H and I of the ternary diagram of FIG. 3. Points E, F, G, H, and I of FIG. 3 have the following values for "q", "r", "s" and "t"

| | Mole Fraction | | |
|---|---|---|---|
| | r | s | (t + q) |
| F | 0.60 | 0.37 | 0.03 |
| G | 0.37 | 0.60 | 0.03 |
| H | 0.01 | 0.60 | 0.39 |
| I | 0.01 | 0.01 | 0.98 |
| J | 0.60 | 0.01 | 0.39 |

For reasons unknown at present, not every reaction mixture gave crystalline CoMnAPSO products when reaction products were examined for CoMnAPSO products by X-ray analysis. Those reaction mixtures from which crystalline CoMnAPSO products were obtained are reported in the examples hereinafter as numbered examples and those reaction mixtures from which CoMnAPSO products were not identified by use of X-ray analysis are reported as lettered examples.

In the foregoing expression of the reaction composition, the reactants are normalized with respect to the total of "o", "p", "r", "s" and "t" such that (o+p+r+s+t)=1.00 mole, whereas in the examples the reaction mixtures are expressed in terms of molar oxide ratios and may be normalized to the moles of $P_2O_5$. This latter form is readily converted to the former form by routine calculations by dividing the number of moles of each component and water by the total number of moles of cobalt, magnesium, aluminum, phosphorus and silicon.

In forming the reaction mixture from which the instant molecular sieves are formed the organic templating agent, i.e., "template", can be any of those heretofore proposed for use in the synthesis of conventional zeolite aluminosilicates. In general these compounds contain elements of Group VA of the Periodic Table of Elements, particularly nitrogen, phosphorus, arsenic and antimony, preferably nitrogen or phosphorous and most preferably nitrogen, where such compounds also contain at least one alkyl or aryl group having from 1 to 8 carbon atoms. Particularly preferred compounds for use as templating agents are the amines, quaternary phosphonium compounds and quaternary ammonium compounds, the latter two being represented generally by the formula $R_4X^+$ wherein "X" is nitrogen or phosphorus and each R is an alkyl or aryl group containing from 1 to 8 carbon atoms. Polymeric quarternary ammonium salts such as $[C_{14}H_{32}N_2)(OH)_2]_x$ wherein "x" has a value of at least 2 are also suitably employed. The mono-, di- and tri-amines are advantageously utilized, either alone or in combination with a quarternary ammonium compound or other templating compound. Mixtures of two or more templating agents can either produce mixtures of the desired CoMnAPSOs or the more strongly directing templating species may control the course of the reaction with the other templating agents serving primarily to establish the pH conditions of the reaction gel. Representative templating agents include tetramethylammonium; tetraethylammonium; tetrapropylammonium; tetrabutylammonium ions; tetrapentylammonium ion; di-n-propylamine; tri-n-propylamine; triethylamine; triethanolamine; piperidine; cyclohexylamine; 2-methylpyridine; N,N-dimethylbenzylamine; N,N-dimethylethanolamine; choline; N,N'-dimethylpiperazine; 1,4-diazabicyclo (2,2,2,) octane; N-methyldiethanol-amine; N-methylethanolamine; N-methylpiperidine; 3-methyl-N-methylpiperidine; N-methylcyclohexylamine; 3-methylpyridine; 4-methylpyridine; quinuclidine; N,N'-dimethyl-1,4-diazabicyclo (2,2,2,) octane ion; di-n-butylamine, neopentylamine; di-n-pentylamine; isopropylamine; t-butylamine; ethylenediamine; pyrrolidine; and 2-imidazolidone. Not every templating agent will direct the formation of every species of CoMnAPSO, i.e., a single templating agent can, with proper manipulation of the reaction conditions, direct the formation of several CoMnAPSO compositions, and a given CoMnAPSO composition can be produced using several different templating agents.

The source of silicon may be silica, either as a silica sol or as fumed silica, a reactive solid amorphous precipitated silica, silica gel, alkoxides of silicon, silicic acid or alkali metal silicate and mixtures thereof.

The most suitable phosphorus source yet found for the instant process is phosphoric acid, but organic phosphates such as triethyl phosphate have been found satisfactory, and so also have crystalline or amorphous aluminophosphates such as the $AlPO_4$ composition of U.S. Pat. No. 4,310,440. Organo-phosphorus compounds, such as tetrabutylphosphonium bromide, do not, apparently, serve as reactive sources of phosphorus, but these compounds may function as templating agents, although it is believed that such may be transformed in situ to reactive sources of phosphorus under suitable process conditions. Conventional phosphorus salts such as sodium metaphosphate, may be used, at least in part, as the phosphorus source, but are not preferred.

The preferred aluminum source is either an aluminum alkoxide, such as aluminum isoproproxide, or pseudoboehmite. The crystalline or amorphous aluminophosphates which are a suitable source of phosphorus are, of course, also suitable sources of aluminum. Other sources of aluminum used in zeolite synthesis, such as gibbsite, sodium aluminate and aluminum trichloride, can be employed but are not preferred.

The reactive sources of cobalt and manganese can be introduced into the reaction system in any form which permits the formation in situ of the reactive form cobalt and manganese, i.e., reactive to form the framework tetrahedral units of cobalt and manganese. Compounds of cobalt and manganese which may be employed include oxides, hydroxides, alkoxides, nitrates, sulfates, carboxylates (e.g. acetates) and halides and include: cobalt chloride hexahydrate, alpha cobaltous iodide, cobaltous sulfate, cobalt acetate, cobaltous bromide, cobaltous chloride, manganous acetate, manganous bromide, manganous sulfate, and the like.

While not essential to the synthesis of CoMnAPSO compositions, stirring or other moderate agitation of the reaction mixture and/or seeding the reaction mixture with seed crystals of either the CoMnAPSO species to be produced or a topologically similar aluminophosphate, aluminosilicate or other molecular sieve composition facilitates the crystallization procedure.

After crystallization the CoMnAPSO product may be isolated and advantageously washed with water and dried in air. The as-synthesized CoMnAPSO contains within its internal pore system at least one form of the templating agent, referred to herein as the "organic moiety", employed in its formation. Most commonly the organic moiety is present, at least in part, as a charge-balancing cation as is generally the case with as-synthesized aluminosilicate zeolites prepared from organic-containing reaction systems. It is possible, however, that some or all of any organic moiety may be an occluded molecular species in a particular CoMnAPSO species. As a general rule the templating agent, and hence any occluded organic species, is too large to move freely through the pore system of the CoMnAPSO product and must be removed by calcining the CoMnAPSO at temperatures of from 200° C. to 700° C. to thermally degrade the organic species. In a few instances the pores of the CoMnAPSO product are sufficiently large to permit transport of the templating agent, particularly if the latter is a small molecule, and accordingly complete or partial removal thereof can be accomplished by conventional desorption procedures such as carried out in the case of zeolites. It will be understood that the term "as-synthesized" as used herein does not include the condition of the CoMnAPSO species wherein the organic moiety occupying the intracrystalline pore system as a result of the hydrothermal crystallization process has been reduced by post-synthesis treatment such that the value of "m" in the composition formula:

mR:(Co$_u$Mn$_v$Al$_x$P$_y$Si$_z$)O$_2$ has a value of less than 0.02. The other symbols of the formula are as defined hereinabove. In those preparations in which an alkoxide is employed as the source of cobalt, manganese, aluminum, phosphorus and/or silicon, the corresponding alcohol is necessarily present in the reaction mixture since it is a hydrolysis product of the alkoxide. It has not been determined whether this alcohol participates in the synthesis process as a templating agent. For the purposes of this application, however, this alcohol is arbitrarily omitted from the class of templating agents, even if it is present in the as-synthesized CoMnAPSO material.

Since the present CoMnAPSO compositions are formed from CoO$_2$, MnO$_2$, AlO$_2$, PO$_2^+$, and SiO$_2$ tetrahedral units which, respectively, have net charges of $-2$ and/or $-1$, $-2$, $-1$, $+1$, and 0, the matter of cation exchangeability is considerably more complicated than in the case of zeolitic molecular sieves in which, ideally, there is a stoichiometric relationship between AlO$_2^-$ tetrahedra and charge-balancing cations. In the instant compositions, an AlO$_2^-$ tetrahedron can be balanced electrically either by association with a PO$_2^+$ tetrahedron or a simple cation such as an alkali metal cation, a proton (H$^+$), a cation of cobalt and/or manganese present in the reaction mixture, or an organic cation derived from the templating agent. Similarly, CoO$_2^-$, CoO$_2^{-2}$ and MnO$_2^{-2}$ tetrahedran can be balanced electrically by association with PO$_2^+$ tetrahedra, a simple cation such as an alkali metal cation, a proton (H$^+$), a cation of cobalt and/or manganese, organic cations derived from the templating agent, or other divalent or polyvalent metal cations introduced from an extraneous source. It has also been postulated that non-adjacent AlO$_2^-$ and PO$_2^+$ tetrahedral pairs can be balanced by Na$^+$ and OH$^-$ respectively [Flanigen and Grose, Molecular Sieve Zeolites-I, ACS, Washington, DC (1971)]

The CoMnAPSO compositions of the present invention exhibit cation-exchange capacity when analyzed using ion-exchange techniques heretofore employed with zeolitic aluminosilicates and have pore diameters which are inherent in the lattice structure of each species and which are at least about 3 Å in diameter. Ion exchange of CoMnAPSO compositions will ordinarily be possible only after the organic moiety present as a result of synthesis has been removed from the pore system. Dehydration to remove water present in the as-synthesized CoMnAPSO compositions can usually be accomplished, to some degree at least, in the usual manner without removal of the organic moiety, but the absence of the organic species greatly facilitates adsorption and desorption procedures. As illustrated hereinafter, the CoMnAPSO materials have various degrees of hydrothermal and thermal stability, some being quite remarkable in this regard, and will function as molecular sieve adsorbents and hydrocarbon conversion catalysts or catalyst bases.

In each example the stainless steel reaction vessel utilized was lined with the inert plastic material, polytetrafluoroethylene, to avoid contamination of the reaction mixture. In general, the final reaction mixture from which each CoMnAPSO composition is crystallized is prepared by forming mixtures of less than all of the reagents and thereafter incorporating into these mixtures additional reagents either singly or in the form of other intermediate mixtures of two or more reagents. In some instances the reagents admixed retain their identity in the intermediate mixture and in other cases some or all of the reagents are involved in chemical reactions to produce new reagents. The term "mixture" is applied in both cases. Further, unless otherwise specified, each intermediate mixture as well as the final reaction mixture was stirred until substantially homogeneous.

Where reaction products are subjected to X-ray analysis, the X-ray patterns are obtained using standard X-ray powder diffraction techniques. The radiation source is a high-intensity, copper target, X-ray tube operated at 50 Kv and 40 ma. The diffraction pattern from the copper K-α radiation and graphite monochromator is suitably recorded by an X-ray spectrometer scintillation counter, pulse height analyzer and strip chart recorder. Flat compressed powder samples are scanned at 2° (2 theta) per minute, using a two second time constant. Interplanar spacings (d) in Angstrom units are obtained from the position of the diffraction peaks expressed as 2θ where θ is the Bragg angle as observed on the strip chart. Intensities are determined from the heights of diffraction peaks after subtracting background, "$I_o$" being the intensity of the strongest line or peak, and "I" being the intensity of each of the other peaks.

Alternatively, the X-ray patterns are obtained from the copper K-alpha radiation by use of computer based techniques using Siemens D-500 X-ray powder diffractometers, Siemens Type K-805 X-ray sources, available from Siemens Corporation, Cherry Hill, NJ, with appropriate computer interface.

As will be understood by those skilled in the art the determination of the parameter 2 theta is subject to both human and mechanical error, which in combination, can impose an uncertainty of about ±0.4° (denotes plus or minus 0.4°) on each reported value of 2 theta. This uncertainty is, of course, also manifested in the reported values of the d-spacings, which are calculated from the 2 theta values. This imprecision is general throughout the art and is not sufficient to preclude the differentiation of the present crystalline materials from each other and from the compositions of the prior art. In some of the X-ray patterns reported, the relative intensities of the d-spacings are indicated by the notations vs, s, m, w and vw which represent very strong, strong, medium, weak and very weak, respectively.

In certain instances the purity of a synthesized product may be assessed with reference to its X-ray powder diffraction pattern. Thus, for example, if a sample is stated to be pure, it is intended only that the X-ray pattern of the sample is free of lines attributable to crystalline impurities, not that there are no amorphous materials present.

The molecular sieves of the instant invention may be characterized by their x-ray powder diffraction patterns and such may have one of the x-ray patterns set forth in the following Tables A, B and C, wherein said x-ray patterns are for both the as-synthesized and calcined forms unless otherwise noted:

TABLE A

| 2θ | (CoMnAPSO-5) d(Å) | Relative Intensity |
|---|---|---|
| 7.4–7.5 | 11.95–11.84 | m |
| 12.9–13.1 | 6.89–6.76 | w–m |
| 14.9 | 5.93 | vw–w |
| 19.7–19.8 | 4.51–4.49 | vw–w |
| 20.9–21.3 | 4.26–4.17 | m |
| 22.4–22.5 | 3.97–3.95 | m |

TABLE B

| 2θ | (CoMnAPSO-11) d(Å) | Relative Intensity |
|---|---|---|
| 9.5–9.6 | 9.31–9.21 | m–vs |
| 15.7–15.9 | 5.64–5.57 | m–vs |
| 20.3–20.4 | 4.37–4.36 | m |
| 21.1–21.2 | 4.21–4.19 | m |
| 22.1–22.5 | 4.02–3.95 | m |
| 23.2–23.4 | 3.83–3.80 | vs |

TABLE C

| 2θ | (CoMnAPSO-34) d(Å) | Relative Intensity |
|---|---|---|
| 9.5–9.6 | 9.29–9.20 | vs |
| 12.8–13.0 | 6.92–6.81 | w–m |
| 16.0–16.2 | 5.54–5.48 | vw–m |
| 20.6–20.9 | 4.32–4.26 | m |
| 21.1–21.2 | 4.22–4.20 | m |
| 25.2–25.3 | 3.530–3.520 | vw–w |
| 31.0–31.5 | 2.881–2.840 | w |

The following examples are provided to further illustrate the invention and are not intended to be limiting thereof:

PREPARATIVE REAGENTS

In the following examples the CoMnAPSO compositions were prepared using numerous regents. The reagents employed and abbreviations employed herein, if any, for such reagents are as follows:

(a) Alipro: aluminum isopropoxide;

(b) LUDOX-LS: LUDOX-LS is the tradename of DuPont for an aqueous solution of 30 weight percent $SiO_2$ and 0.1 weight percent $Na_2O$;

(c) $H_3PO_4$: 85 weight percent phosphoric acid;

(d) MnAc: Manganese acetate, $Mn(C_2H_3O_2)_2.4H_2O$;

(e) CoAc: Cobalt Acetate, $Co(C_2H_3O_2)_2.4H_2O$;

(f) TEAOH: 40 weight percent aqueous solution of tetraethylammonium hydroxide; and (g) $Pr_2NH$: di-n-propylamine, $(C_3H_7)_2NH$.

PREPARATIVE PROCEDURES

The following preparative examples were carried out by forming a starting reaction mixture by adding the $H_3PO_4$ and one half of the quantity of water. To this mixture the aluminum isopropoxide was added. This mixture was then blended until a homogeneous mixture was observed. To this mixture the LUDOX-LS was added and the resulting mixture blended (about 2 minutes) until a homogeneous mixture was observed. A second mixture was prepared using manganese acetate and one half of the remaining water. A third mixture was prepared using cobalt acetate and one half of the remaining water. The three mixtures were admixed and the resulting mixture blended until a homogeneous mixture was observed. The organic templating agent was then added to the resulting mixture and the resulting mixture blended until a homogeneous mixture was observed, i.e. about 2 to 4 minutes. The pH of the mixture was measured and adjusted for temperature. The mixture was then placed in a lined (polytetrafluoroethylene) stainless steel pressure vessel and digested at a temperature. All digestions were carried out at the autogeneous pressure.

EXAMPLES 1 TO 4

CoMnAPSO molecular sieves were prepared according to the above identified procedure and the CoMnAPSO products determined by X-ray analysis. The results of examples 1 to 4 are set forth in Table I. Examples A to F in Table I represent reaction mixtures that did not show CoMnAPSO products when determined by X-ray analysis.

TABLE I

| Example[1] | Template | Temp (°C.) | Time(days) | CoMnMqAPSO Product(s)[2] |
|---|---|---|---|---|
| 1 | TEAOH | 150 | 2 | CoMnAPSO-34; CoMnAPSO-5 |
| 2 | TEAOH | 150 | 7 | CoMnAPSO-34; CoMnAPSO-5 |
| 3 | $Pr_2NH$ | 200 | 2 | CoMnAPSO-5; CoMnAPSO-11 |
| 4 | $Pr_2NH$ | 200 | 7 | CoMnAPSO-5; CoMnAPSO-11 |
| A | TEAOH | 100 | 3 | — |
| B | TEAOH | 100 | 7 | — |
| C | $Pr_2NH$ | 150 | 2 | — |
| D[3] | $Pr_2NH$ | 150 | 10 | — |
| E[3] | $Pr_2NH$ | 150 | 6 | — |
| F[3] | $Pr_2NH$ | 150 | 15 | — |

[1]The reaction mixture comprised: $1.0R:0.2\ MnO:0.2\ CoO:0.8\ Al_2O_3:0.8\ P_2O_5:0.4\ SiO_2:50\ H_2O$ where "R" is the template.
[2]Major species as identified by X-ray powder diffraction pattern of product, except that when two species are identified the first species listed is present in an amount equal to or greater than the second species listed. A "—" indicates that crystalline products were not identified by X-ray analysis.
[3]X-ray analysis indicated that crystalline product was beginning to form.

EXAMPLE 5

(a) Samples of the above prepared CoMnAPSO products, as identified in parenthesis, were calcined in air to remove at least part of the organic templating agent of the CoMnAPSO product. The adsorption capacities of each calcined sample were measured using a standard McBain-Bakr gravimetric adsorption apparatus. The samples were activated in a vacuum (less than 0.04 torr) at 350° C. prior to measurement. The McBain-Bakr data were as follows:

(b) CoMnAPSO-34 and CoMnAPSO-5 (Example 2):

| Adsorbate | Kinetic Diameter, Å | Pressure (Torr) | Temp (°C.) | Wt. % Adsorbed* |
|---|---|---|---|---|
| Oxygen | 3.46 | 105 | −183 | 13.8 |
| Oxygen | 3.46 | 733 | −183 | 18.5 |
| Neopentane | 6.2 | 742 | 23.8 | 2.6 |
| Cyclohexane | 6.0 | 65 | 23.7 | 4.6 |
| n-hexane | 4.3 | 93 | 23.4 | 5.0 |
| $H_2O$ | 2.65 | 4.6 | 23.4 | 15.8 |
| $H_2O$ | 2.65 | 19 | 23.7 | 23.6 |

*calcined in air at 600° C. for one hour prior to activation (c) CoMnAPSO-5 and CoMnAPSO-11 (Example 4):

| Adsorbate | Kinetic Diameter, Å | Pressure (Torr) | Temp (°C.) | Wt. % Adsorbed* |
|---|---|---|---|---|
| Oxygen | 3.46 | 105 | −183 | 5.5 |
| Oxygen | 3.46 | 733 | −183 | 9.3 |
| Neopentane | 6.2 | 742 | 23.8 | 2.4 |
| Cyclohexane | 6.0 | 65 | 23.7 | 5.9 |
| $H_2O$ | 2.65 | 4.6 | 23.4 | 7.4 |
| $H_2O$ | 2.65 | 19 | 23.7 | 16.2 |

*calcined in air at 600° C. for one hour prior to activation

EXAMPLE 6

Samples of the as-synthesized products of examples 2 and 4 were subjected to chemical analysis. The chemical analysis for these CoMnAPSOs was:

(a) The chemical analysis for the product of example 2 was:

| Component | Weight Percent |
|---|---|
| $Al_2O_3$ | 27.5 |
| $P_2O_5$ | 37.7 |
| $SiO_2$ | 4.98 |
| CoO | 4.3 |
| MnO | 5.2 |
| Carbon | 5.3 |
| LOI* | 20.5 |

*Loss on Ignition

The above chemical analysis gives an overall product composition in molar oxide ratios (anhydrous basis) of:

$$0.057CoO:0.073MnO:0.270Al_2O_3:0.266P_2O_5:0.083SiO_2$$

and a formula (anhydrous basis) of:

$$0.055R(Al_{0.420}P_{0.414}Si_{0.065}Co_{0.044}Mn_{0.057})O_2$$

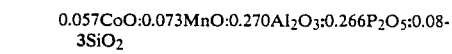

(b) The chemical analysis for the product of example 4 was:

| Component | Weight Percent |
|---|---|
| $Al_2O_3$ | 26.6 |
| $P_2O_5$ | 37.6 |
| $SiO_2$ | 7.1 |
| CoO | 5.1 |
| MnO | 6.0 |
| Carbon | 1.91 |
| LOI* | 17.9 |

*Loss on Ignition

The above chemical analysis gives an overall product composition in molar oxide ratios (anhydrous basis) of:

$$0.068CoO:0.085MnO:0.261Al_2O_3:0.265P_2O_5:0.118SiO_2$$

and a formula (anhydrous basis) of:

$$0.027R(Al_{0.40}P_{0.40}Si_{0.089}Co_{0.051}Mn_{0.064})O_2$$

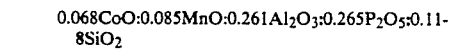

EXAMPLE 7

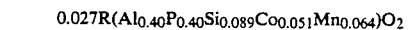

EDAX (energy dispersive analysis by x-ray) microprobe analysis in conjunction with SEM (scanning electron microscope) was carried out on the products of examples 2 and 4. Analysis of crystals having a morphology characteristic of each CoMnAPSO product gave the following analysis based on relative peak heights:

(a) Example 2 (CoMnAPSO-5):

| Average of Spot Probes | |
|---|---|
| Al | 0.81 |
| P | 0.98 |
| Si | 0.18 |
| Co | 0.10 |
| Mn | 0.17 |

(b) Example 2 (CoMnAPSO-34):

| Average of Spot Probes | |
|---|---|
| Al | 0.82 |
| P | 0.93 |
| Si | 0.17 |
| Co | 0.03 |
| Mn | 0.03 |

(c) Example 4 (CoMnAPSO-5):

| Average of Spot Probes | |
|---|---|
| Al | 0.93 |
| P | 0.71 |
| Si | 0.15 |
| Co | 0.05 |
| Mn | 0.07 |

(d) Example 4 (CoMnAPSO-11):

| Average of Spot Probes | |
|---|---|
| Al | 0.81 |
| P | 0.95 |
| Si | 0.15 |
| Co | 0.03 |
| Mn | 0.05 |

EXAMPLE 8

(a) CoMnAPSO-5, as prepared in example 1, was subjected to x-ray analysis. The CoMnAPSO-5 was determined to have an x-ray powder diffraction pattern characterized by the following data:

| 2θ | d (Å) | (I/Io) × 100 |
|---|---|---|
| 7.5 | 11.84 | 67 |
| 9.5* | 9.29 | 100 |
| 12.9** | 6.89 | 11 |
| 14.1* | 6.29 | 7 |
| 14.9 | 5.93 | 14 |
| 16.0* | 5.54 | 22 |
| 18.0* | 4.93 | 10 |
| 19.8 | 4.49 | 19 |
| 20.6* | 4.32 | 51 |
| 21.1** | 4.22 | 40 |
| 22.4 | 3.96 | 28 |
| 25.2* | 3.530 | 12 |
| 29.1 | 3.071 | 6 |
| 29.5* | 3.024 | 3 |
| 30.1 | 2.968 | 10 |
| 30.5* | 2.928 | 16 |
| 31.3* | 2.862 | 11 |
| 33.7* | 2.659 | 3 |
| 34.5 | 2.601 | 4 |
| 34.6* | 2.591 | 5 |
| 37.8 | 2.383 | 6 |
| 47.7** | 1.905 | 3 |
| 48.9* | 1.863 | 2 |
| 49.9* | 1.828 | 2 |
| 50.9* | 1.794 | 2 |

-continued

| 2θ | d (Å) | (I/Io) × 100 |
|---|---|---|
| 55.8 | 1.647 | 2 |

*peak may be an impurity
**impurity peak and CoMnMgAPSO-5

(b) A portion of the as-synthesized CoMnAPSO-5 of example 2 was calcined in air at 600° C. for one (1) hour. The calcined product was characterized by the following x-ray powder diffraction pattern:

| 2θ | d(Å) | (I/Io) × 100 |
|---|---|---|
| 7.5 | 11.84 | 32 |
| 9.6* | 9.20 | 100 |
| 13.0** | 6.81 | 20 |
| 14.9 | 5.93 | 4 |
| 16.2* | 5.48 | 8 |
| 18.0* | 4.93 | 6 |
| 19.3* | 4.60 | 3 |
| 19.8 | 4.49 | 8 |
| 20.9** | 4.26 | 22 |
| 21.2** | 4.20 | 26 |
| 21.5* | 4.13 | 3 |
| 22.5 | 3.95 | 32 |
| 23.4* | 3.81 | 3 |
| 25.3* | 3.520 | 7 |
| 26.1 | 3.420 | 11 |
| 26.2* | 3.396 | 7 |
| 28.5* | 3.129 | 3 |
| 29.2 | 3.063 | 6 |
| 30.2 | 2.965 | 6 |
| 31.0* | 2.881 | 11 |
| 31.5* | 2.840 | 7 |
| 34.7 | 2.584 | 4 |
| 34.9 | 2.568 | 3 |
| 38.0* | 2.368 | 2 |

*peak may be an impurity
**impurity peak and CoMnAPSO-5

(c) The species CoMnAPSO-5 is a molecular sieve having a characteristic x-ray powder diffraction pattern which contains at least the d-spacings set forth in Table II as follows:

TABLE II

| 2θ | d (Å) | Relative Intensity |
|---|---|---|
| 7.4–7.5 | 11.9–11.84 | m |
| 12.9–13.1 | 6.89–6.76 | w–m |
| 14.9 | 5.93 | vw–w |
| 19.7–19.8 | 4.51–4.49 | vw–w |
| 20.9–21.3 | 4.26–4.17 | m |
| 22.4–22.5 | 3.97–3.95 | m |

(d) All of the CoMnAPSO-5 compositions, both as-synthesized and calcined, for which x-ray powder diffraction data have been obtained have patterns which are within the generalized pattern of Table III, below:

TABLE III

| 2θ | d (Å) | (I/Io) × 100 |
|---|---|---|
| 7.4–7.5 | 11.95–11.84 | 32–67 |
| 12.9–13.1 | 6.89–6.81 | 11–20 |
| 14.9 | 5.93 | 4–14 |
| 19.7–19.8 | 4.51–4.49 | 8–19 |
| 20.9–21.3 | 4.26–4.17 | 22–40 |
| 22.4–22.5 | 3.96–3.95 | 28–32 |
| 24.7–24.8 | 3.60–3.59 | 6 |
| 25.9–26.1 | 3.440–3.420 | 10–11 |
| 29.0–29.2 | 3.079–3.063 | 6 |
| 29.9–30.2 | 2.988–2.965 | 6–10 |
| 34.4–34.7 | 2.607–2.584 | 4 |
| 34.9 | 2.568 | 3 |
| 37.8 | 2.383 | 6 |
| 47.7 | 1.905 | 3 |

TABLE III-continued

| 2Θ | d (Å) | (I/Io) × 100 |
|---|---|---|
| 55.8 | 1.647 | 2 |

EXAMPLE 9

(a) The CoMnAPSO-11, prepared in example 3, was subjected to X-ray analysis. The CoMnAPSO-11 was impure but the CoMnAPSO-11 was determined to have an X-ray powder diffraction pattern characterized by the following data:

| 2Θ | d (Å) | (I/Io) × 100 |
|---|---|---|
| 7.0* | 12.56 | 12 |
| 7.5* | 11.86 | 68 |
| 8.1 | 10.88 | 46 |
| 9.5 | 9.31 | 68 |
| 12.9* | 6.87 | 11 |
| 13.2 | 6.73 | 24 |
| 14.9* | 5.95 | 12 |
| 15.7 | 5.64 | 49 |
| 16.3 | 5.44 | 9 |
| 19.0 | 4.67 | 9 |
| 19.7* | 4.50 | 29 |
| 20.4 | 4.36 | 66 |
| 21.1** | 4.21 | 37 |
| 21.2 | 4.19 | 34 |
| 22.4* | 3.96 | 41 |
| 22.8 | 3.91 | 29 |
| 23.2 | 3.83 | 100 |
| 24.8** | 3.59 | 10 |
| 25.9* | 3.443 | 23 |
| 26.5 | 3.365 | 32 |
| 28.2 | 3.163 | 9 |
| 28.7 | 3.113 | 25 |
| 29.5 | 3.024 | 8 |
| 29.9* | 2.985 | 15 |
| 31.5 | 2.838 | 8 |
| 32.7 | 2.739 | 2 |
| 34.2 | 2.622 | 2 |
| 36.4 | 2.468 | 2 |
| 37.6 | 2.392 | 2 |

*peak may be an impurity
**impurity peak (b) A portion of the as-synthesized CoMnAPSO-11 of example 4 was calcined in air at 600° C. for one (1) hour. The calcined product was characterized by the following X-ray powder diffraction pattern:

| 2Θ | d (Å) | (I/Io) × 100 |
|---|---|---|
| 7.5* | 11.86 | 95 |
| 8.2 | 10.85 | 68 |
| 9.6 | 9.19 | 95 |
| 13.1* | 6.77 | 45 |
| 15.9 | 5.58 | 91 |
| 19.8* | 4.48 | 32 |
| 20.3 | 4.37 | 49 |
| 21.3* | 4.17 | 34 |
| 22.5** | 3.96 | 62 |
| 23.4 | 3.80 | 100 |
| 26.0* | 3.423 | 43 |
| 26.4 | 3.376 | 40 |
| 26.6 | 3.346 | 16 |
| 29.1* | 3.073 | 27 |
| 29.2 | 3.061 | 28 |
| 30.2* | 2.962 | 21 |
| 32.8 | 2.732 | 21 |
| 32.9 | 2.719 | 31 |
| 34.7* | 2.586 | 28 |
| 36.2 | 2.481 | 2 |

*peak may contain impurity
**impurity peak (c) The species CoMnAPSO-11 is a molecular sieve having a characteristic x-ray powder diffraction pattern which contains at least the d-spacings set forth in Table IV as follows:

TABLE IV

| 2Θ | d, (Å) | Relative Intensity |
|---|---|---|
| 9.5–9.6 | 9.31–9.21 | m–vs |
| 15.7–15.9 | 5.64–5.57 | m–vs |
| 20.3–20.4 | 4.37–4.36 | m |
| 21.1–21.2 | 4.21–4.19 | m |
| 22.1–22.5 | 4.02–3.95 | m |
| 23.2–23.4 | 3.83–3.80 | vs |

(d) All of the CoMnAPSO-11 compositions both as-synthesized and calcined, for which x-ray powder diffraction data have presently been obtained have patterns which are within the generalized pattern of Table V, below:

TABLE V

| 2Θ | d, (Å) | (I/Io) × 100 |
|---|---|---|
| 8.1–8.2 | 10.88–10.85 | 46–68 |
| 9.5–9.6 | 9.31–9.19 | 68–95 |
| 13.1–13.2 | 6.77–6.73 | 24–45 |
| 15.7–15.9 | 5.64–5.58 | 49–91 |
| 16.3 | 5.44 | 9 |
| 19.0 | 4.67 | 9–10 |
| 20.3–20.4 | 4.37–4.36 | 49–66 |
| 21.1–21.2 | 4.21–4.19 | 30–37 |
| 22.1–22.5 | 4.02–3.96 | 31–62 |
| 22.7–22.8 | 3.92–3.91 | 28–29 |
| 23.2–23.4 | 3.83–3.80 | 100 |
| 24.7–24.8 | 3.60–3.59 | 10–14 |
| 26.4–26.6 | 3.376–3.346 | 16–40 |
| 28.1–28.2 | 3.175–3.163 | 9 |
| 28.7 | 3.113 | 25–26 |
| 29.2–29.5 | 3.061–3.024 | 8–28 |
| 31.5 | 2.838 | 8 |
| 32.7–32.8 | 2.739–2.732 | 2–27 |
| 32.9 | 2.719 | 31 |
| 34.2 | 2.622 | 2–11 |
| 36.2–36.4 | 2.481–2.468 | 2–9 |
| 37.6–37.9 | 2.392–2.374 | 2–3 |

EXAMPLE 10

(a) The CoMnAPSO-34, prepared in example 1, was subjected to x-ray analysis. The CoMnAPSO-34 was impure but was the major phase and was determined to have an x-ray powder diffraction pattern characterized by the following data:

| 2Θ | d (Å) | (I/Io) × 100 |
|---|---|---|
| 7.5* | 11.84 | 67 |
| 9.5 | 9.29 | 100 |
| 12.9** | 6.89 | 11 |
| 14.1 | 6.29 | 7 |
| 14.9* | 5.93 | 14 |
| 16.0 | 5.54 | 22 |
| 18.0 | 4.93 | 10 |
| 19.8* | 4.49 | 19 |
| 20.6 | 4.32 | 51 |
| 21.1** | 4.22 | 40 |
| 22.4* | 3.96 | 28 |
| 25.2 | 3.530 | 12 |
| 29.1* | 3.071 | 6 |
| 29.5 | 3.024 | 3 |
| 30.1* | 2.968 | 10 |
| 30.5 | 2.928 | 16 |
| 31.3 | 2.862 | 11 |
| 33.7 | 2.659 | 3 |
| 34.5* | 2.601 | 4 |
| 34.6 | 2.591 | 5 |
| 37.8* | 2.383 | 6 |
| 47.7** | 1.905 | 3 |

-continued

| 2Θ | d (Å) | (I/Io) × 100 |
|---|---|---|
| 48.9 | 1.863 | 2 |
| 49.9 | 1.828 | 2 |
| 50.9 | 1.794 | 2 |
| 55.8* | 1.647 | 2 |

*peak may contain impurity
**impurity peak (b) A portion of the as-synthesized CoMnAPSO-34 of 2 was calcined in air at 600° C. for one (1) hour. The calcined product was characterized by the following x-ray powder diffraction pattern:

| 2Θ | d (Å) | (I/Io) × 100 |
|---|---|---|
| 7.5* | 11.84 | 32 |
| 9.6 | 9.20 | 100 |
| 13.0** | 6.81 | 20 |
| 14.9* | 5.93 | 4 |
| 16.2 | 5.48 | 8 |
| 18.0 | 4.93 | 6 |
| 19.3 | 4.60 | 3 |
| 19.8* | 4.49 | 8 |
| 20.9** | 4.26 | 22 |
| 21.2** | 4.20 | 26 |
| 21.5 | 4.13 | 3 |
| 22.5* | 3.96 | 32 |
| 23.4 | 3.81 | 3 |
| 25.3 | 3.520 | 7 |
| 26.1* | 3.420 | 11 |
| 26.2 | 3.396 | 7 |
| 28.5 | 3.129 | 3 |
| 29.2* | 3.063 | 6 |
| 30.2* | 2.965 | 6 |
| 31.0 | 2.881 | 11 |
| 31.5 | 2.840 | 7 |
| 34.7* | 2.584 | 4 |
| 34.9* | 2.568 | 3 |
| 38.0 | 2.368 | 2 |

*peak may contain impurity
**impurity peak (c) The species CoMnAPSO-34 is a molecular sieve having a characteristic x-ray powder diffraction pattern which contains at least the d-spacings set forth in Table VI as follows:

TABLE VI

| 2Θ | d, (Å) | Relative Intensity |
|---|---|---|
| 9.5–9.6 | 9.29–9.20 | vs |
| 12.8–13.0 | 6.92–6.81 | w–m |
| 16.0–16.2 | 5.54–5.48 | vw–m |
| 20.6–20.9 | 4.32–4.26 | m |
| 21.1–21.2 | 4.22–4.20 | m |
| 25.2–25.3 | 3.530–3.520 | vw–w |
| 31.0–31.5 | 2.881–2.840 | w |

(d) All of the CoMnAPSO-34 compositions, both as-synthesized and calcined, for which x-ray powder diffraction data have been obtainehave patterns which are within the generalized pattern below:

TABLE VII

| 2Θ | d (Å) | (I/Io) × 100 |
|---|---|---|
| 9.5–9.6 | 9.29–9.20 | 100 |
| 12.8–13.0 | 6.92–6.81 | 11–20 |
| 14.1 | 6.29 | 7–9 |
| 16.0–16.2 | 5.54–5.48 | 8–23 |
| 18.0 | 4.93 | 6–12 |
| 19.3 | 4.60 | 3 |
| 20.6–20.9 | 4.32–4.26 | 22–57 |
| 21.1–21.2 | 4.22–4.20 | 26–40 |
| 21.5 | 4.13 | 3 |
| 23.0–23.4 | 3.87–3.81 | 2–3 |
| 25.2–25.3 | 3.530–3.520 | 7–14 |
| 25.8–26.2 | 3.453–3.396 | 7–13 |
| 27.5 | 3.243 | 2 |
| 28.3–28.5 | 3.153–3.129 | 3–4 |
| 29.5 | 3.024 | 3 |
| 30.5 | 2.928 | 16–18 |
| 31.0–31.5 | 2.881–2.840 | 11–13 |
| 33.7–33.8 | 2.659–2.652 | 2–7 |
| 34.5–34.6 | 2.601–2.592 | 5 |
| 38.0 | 2.368 | 2 |
| 39.6 | 2.276 | 2 |
| 43.3 | 2.090 | 2 |
| 47.5–47.7 | 1.914–1.905 | 2–3 |
| 48.9–49.0 | 1.863–1.859 | 2–4 |
| 49.9 | 1.828 | 2 |
| 50.8–50.9 | 1.797–1.794 | 2–3 |

EXAMPLE 15

In order to demonstrate the catalytic activity of the CoMnAPSO compositions, calcined samples of the products of examples 2 and 4, were tested for catalytic cracking. The CoMnAPSO compositions were evaluated for n-butane cracking using a bench-scale apparatus.

The reactor was a cylindrical quartz tube 254 mm. in length and 10.3 mm I.D. In each test the reactor was loaded with particles of the CoMnAPSO which were 20–40 mesh (U.S. std.) in size and in an amount of from 0.5 to 5 grams, the quantity being selected so that the conversion of n-butane was at least 5% and not more than 90% under the test conditions. The CoMnAPSO samples had been previously calcined in air to remove organic materials from the pore system, and were activated in situ in the reactor in a flowing stream of helium at 500° C. for one hour. The feedstock was a helium-n-butane mixture containing 2 mole percent n-butane and was passed through the reactor at a rate of 50 cc./minute. Analysis of the feedstock and the reactor effluent were carried out using conventional gas chromatography techniques. The reactor effluent was analyzed after 10 minutes of on-stream operation.

The pseudo-first-order rate constant ($k_A$) was calculated to determine the relative catalytic activity of each CoMnAPSO composition. The $k_A$ value ($cm^3$/g min) obtained for the CoMnAPSO are set forth below:

| Product of Example No. | Rate Constant ($k_A$)** |
|---|---|
| 2* | 6.9 |
| 4* | 0.8 |

*calcined at 600° C. in air for 1.5 hours prior to activation.
**($Cm^3$/gram minute)

PROCESS APPLICATIONS

The CoMnAPSO compositions of the present invention are, in general, hydrophilic and absorb water preferentially over common hydrocarbon molecules such as paraffins, olefins and aromatic species, e.g., benzene, xylenes and cumene. Thus the present CoMnAPSO compositions as a class are useful as desiccants in such adsorption separation/purification processes as natural gas drying, cracked gas drying. Water is also preferentially adsorbed over the so-called permanent gases such as carbon dioxide, nitrogen, oxygen and hydrogen. These CoMnAPSOs are therefore suitably employed in the drying of reformer hydrogen streams and in the drying of oxygen, nitrogen or air prior to liquification.

In this respect the adsorptive properties of the CoMnAPSOs appears to be quite similar to those of the low silica aluminosilicate zeolites, despite the fact that they exhibit, at best, a modest ion-exchange capacity.

The present CoMnAPSO compositions also exhibit novel surface selectivity characteristics which render them useful as catalyst or catalyst bases in a number of hydrocarbon conversion and oxidative combustion reactions. They can be impregnated or otherwise loaded with catalytically active metals by methods well known in the art and used, for example, in fabricating catalyst compositions having silica or alumina bases. Of the general class, those species having pores larger than about 4Å are preferred for catalytic applications.

Among the hydrocarbon conversion reactions catalyzed by CoMnAPSO compositions are cracking, hydrocracking, alkylation for both the aromatic and isoparaffin types, isomerization including xylene isomerization, polymerization, reforming, hydrogenation, dehydrogenation, transalkylation, dealkylation, hydrodecyclization and dehydrocyclization.

Using CoMnAPSO catalyst compositions which contain a hydrogenation promoter such as platinum or palladium, heavy petroleum residual stocks, cyclic stocks and other hydrocrackable charge stocks, can be hydrocracked at temperatures in the range of 400° F. to 825° F. using molar ratios of hydrogen to hydrocarbon in the range of between 2 and 80, pressures between 10 and 3500 p.s.i.g., and a liquid hourly space velocity (LHSV) of from 0.1 to 20, preferably 1.0 to 10.

The CoMnAPSO catalyst compositions employed in hydrocracking are also suitable for use in reforming processes in which the hydrocarbon feedstocks contact the catalyst at temperatures of from about 700° F. to 1000° F., hydrogen pressures of from 100 to 500 p.s.i.g., LHSV values in the range of 0.1 to 10 and hydrogen to hydrocarbon molar ratios in the range of 1 to 20, preferably between 4 and 12.

These same catalysts, i.e. those containing hydrogenation promoters, are also useful in hydroisomerizations processes in which feedstocks such a normal paraffins are converted to saturated branched chain isomers. Hydroisomerization is carried out at a temperature of from about 200° F. to 600° F., preferably 300° F. to 550° F. with an LHSV value of from about 0.2 to 1.0. Hydrogen is supplied to the reactor in admixture with the hydrocarbon feedstock in molar proportions (hydrogen/hydrocarbon) of between 1 and 5.

At somewhat higher temperatures, i.e. from about 650° F. to 1000° F., preferably 850° F. to 950° F. and usually at somewhat lower pressures within the range of about 15 to 50 p.s.i.g., the same catalyst compositions are used to hydroisomerize normal paraffins. Preferably the paraffin feedstock comprises normal paraffins having a carbon number range of $C_7$–$C_{20}$. Contact time between the feedstock and the catalyst is generally relatively short to avoid undesireable side reactions such as olefin polymerization and paraffin cracking. LHSV values in the range of 0.1 to 10, preferably 1.0 to 6.0 are suitable.

The unique crystal structure of the present CoMnAPSO catalysts and their availability in a form totally void of alkali metal content favor their use in the conversion of alkylaromatic compounds, particularly the catalytic disproportionation of toluene, ethylene, trimethyl benzenes, tetramethyl benzenes and the like. In the disproportionation process, isomerization and transalkylation can also occur. Group VIII noble metal adjuvants alone or in conjunction with Group VI-B metals such as tungsten, molybdenum and chromium are preferably included in the catalyst composition in amounts of from about 3 to 15 weight-% of the overall composition. Extraneous hydrogen can, but need not, be present in the reaction zone which is maintained at a temperature of from about 400° to 750° F., pressures in the range of 100 to 2000 p.s.i.g. and LHSV values in the range of 0.1 to 15.

Catalytic cracking processes are preferably carried out with CoMnAPSO compositions using feedstocks such as gas oils, heavy naphthas, deasphalted crude oil residua, etc., with gasoline being the principal desired product. Temperature conditions of 850° to 1100° F., LHSV values of 0.5 to 10 and pressure conditions of from about 0 to 50 p.s.i.g. are suitable.

Dehydrocyclization reactions employing paraffinic hydrocarbon feedstocks, preferably normal paraffins having more than 6 carbon atoms, to form benzene, xylenes, toluene and the like are carried out using essentially the same reaction conditions as for catalytic cracking. For these reactions it is preferred to use the CoMnAPSO catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 800°–1000° F. are employed at moderate hydrogen pressures of about 300–1000 p.s.i.g., other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like any of which may contain up to about 5 weight-percent of sulfur and up to about 3 weight-percent of nitrogen.

Similar conditions can be employed to effect hydrofining, i.e., denitrogenation and desulfurization, of hydrocarbon feeds containing substantial proportions of organonitrogen and organosulfur compounds. It is generally recognized that the presence of substantial amounts of such constituents markedly inhibits the activity of hydrocracking catalysts. Consequently, it is necessary to operate at more extreme conditions when it is desired to obtain the same degree of hydrocracking conversion per pass on a relatively nitrogenous feed than are required with a feed containing less organonitrogen compounds. Consequently, the conditions under which denitrogenation, desulfurization and/or hydrocracking can be most expeditiously accomplished in any given situation are necessarily determined in view of the characteristics of the feedstocks in particular the concentration of organonitrogen compounds in the feedstock. As a result of the effect of organonitrogen compounds on the hydrocracking activity of these compositions it is not at all unlikely that the conditions most suitable for denitrogenation of a given feedstock having a relatively high organonitrogen content with minimal hydrocracking, e.g., less than 20 volume percent of fresh feed per pass, might be the same as those preferred for hydrocracking another feedstock having a lower concentration of hydrocracking inhibiting constituents e.g., organonitrogen compounds. Consequently, it has become the practice in this art to establish the conditions under which a certain feed is to be contacted on the basis of preliminary screening tests with the specific catalyst and feedstock.

Isomerization reactions are carried out under conditions similar to those described above for reforming, using somewhat more acidic catalysts. Olefins are preferably isomerized at temperatures of 500°–900° F., while paraffins, naphthenes and alkyl aromatics are isomerized at temperatures of 700°–1000° F. Particularly desirable isomerization reactions contemplated herein include the conversion of n-heptene and/or n-octane to isoheptanes, iso-octanes, butane to iso-butane, methylcyclopentane to cyclohexane, meta-xylene and/or ortho-xylene to paraxylene, 1-butene to 2-butene and/or isobutene, n-hexene to isohexene, cyclohexene to methylcyclopentene etc. The preferred form of the catalyst is a combination of the CoMnAPSO with polyvalent metal compounds (such as sulfides) of metals of Group II-A, Group II-B and rare earth metals. For alkylation and dealkylation processes the CoMnAPSO compositions having pores of at least 5Å are preferred. When employed for dealkylation of alkyl aromatics, the temperature is usually at least 350° F. and ranges up to a temperature at which substantial cracking of the feedstock or conversion products occurs, generally up to about 700° F. The temperature is preferably at least 450° F. and not greater than the critical temperature of the compound undergoing dealkylation. Pressure conditions are applied to retain at least the aromatic feed in the liquid state. For alkylation the temperature can be as low as 250° F. but is preferably at least 350° F. In the alkylation of benzene, toluene and xylene, the preferred alkylating agents are olefins such as ethylene and propylene.

What is claimed is:

1. Crystalline molecular sieves having three-dimensional microporous framework structures of $CoO_2$, $MnO_2$, $AlO_2$, $PO_2$ and $SiO_2$ tetrahedral units having an empirical chemical composition on an anhydrous basis expressed by the formula:

mR: $(Co_uMn_vAl_xP_ySi_z)O_2$ wherein "R" represents at least one organic templating agent present in the intracrystalline pore system; "m" represents the amount of "R" present per mole of $(Co_uMn_vAl_xP_ySi_z)O_2$ and has a value of from zero (0) to about 0.3; and "u", "v", "x", "y" and "z", represent the mole fractions of cobalt, manganese, aluminum, phosphorus and silicon, respectively, present as tetrahedral oxides; "w" is the sum of "u+v"; and "w", "x", "y" and "z" are within the pentagonal compositional area defined by points A, B, C, D and E of FIG. 1 and wherein "u", "v", "x", "y", and "z" are at least 0.01.

2. The molecular sieves of claim 1 where "w", "x", "y" and "z" are within the tetragonal compositional area defined by points a, b, c and d of FIG. 2.

3. The crystalline molecular sieves of claim 1 or 2 having a characteristic x-ray powder diffraction pattern which contains at least the d-spacings set forth in the following Table A:

TABLE A

| 2θ | (CoMnAPSO-5) | |
|---|---|---|
| | d (Å) | Relative Intensity |
| 7.4–7.5 | 11.95–11.84 | m |
| 12.9–13.1 | 6.89–6.76 | w–m |
| 14.9 | 5.93 | vw–w |
| 19.7–19.8 | 4.51–4.49 | vw–w |
| 20.9–21.3 | 4.26–4.17 | m |
| 22.4–22.5 | 3.97–3.95 | m |

4. The crystalline molecular sieves of claim 1 or 2 having a characteristic x-ray powder diffraction pattern which contains at least the d-spacings set forth in the following Table B:

TABLE B

| 2θ | (CoMnAPSO-11) | |
|---|---|---|
| | d (Å) | Relative Intensity |
| 9.5–9.6 | 9.31–9.21 | m–vs |
| 15.7–15.9 | 5.64–5.57 | m–vs |
| 20.3–20.4 | 4.37–4.36 | m |
| 21.1–21.2 | 4.21–4.19 | m |
| 22.1–22.5 | 4.02–3.95 | m |
| 23.2–23.4 | 3.83–3.80 | vs |

5. The crystalline molecular sieves of claim 1 or 2 having a characteristic x-ray powder diffraction pattern which contains at least the d-spacings set forth in the following Table C:

TABLE C

| 2θ | CoMnAPSO-34 | |
|---|---|---|
| | d (Å) | Relative Intensity |
| 9.5–9.6 | 9.29–9.20 | vs |
| 12.5–13.0 | 6.92–6.81 | w–m |
| 16.0–16.2 | 5.54–5.48 | vw–m |
| 20.6–20.9 | 4.32–4.26 | m |
| 21.1–21.2 | 4.22–4.20 | m |
| 25.2–25.3 | 3.530–3.520 | vw–w |
| 31.0–31.5 | 2.881–2.840 | w |

6. Molecular sieves prepared by calcining, at a temperature sufficiently high to remove at least some of any organic templating agent present in the intracrystalline pore system the crystalline molecular sieves having three-dimensional microporous framework structures of $CoO_2$, $MnO_2$, $AlO_2$, $PO_2$ and $SiO_2$ tetrahedral oxide units having an empirical chemical composition on an anhydrous basis expressed by the formula:

mR: $(Co_uMn_vAl_xP_ySi_z)O_2$ wherein "R" represents at least one organic templating agent present in the intracrystalline pore system; "m" represents the molar amount of "R" present per mole of $(Co_uMn_vAl_xP_ySi_z)O_2$ and has a value of from zero (0) to about 0.3; and "u", "v", "x", "y" and "z" represent the mole fractions of cobalt, manganese, aluminum, phosphorus and silicon, respectively, present as tetrahedral oxides; "w" is the sum of "u+v"; and "w", "x", "y" and "z" are within the pentagonal compositional area defined by points A, B, C, D and E of FIG. 1 and wherein "u", "v", "x", "y" and "z" are at least 0.01.

7. The crystalline molecular sieves of claims 1 or 2 wherein the values of "u", "v" and "z" have the following mole fraction values: "u" is $\geq 0.044$; "v" is $\geq 0.057$; and "z" is $\geq 0.065$.

* * * * *